United States Patent [19]

Sarges

[11] 4,147,795

[45] Apr. 3, 1979

[54] HYDANTOIN DERIVATIVES AS THERAPEUTIC AGENTS

[75] Inventor: Reinhard Sarges, Mystic, Conn.

[73] Assignee: Pfizer Inc., New York, N.Y.

[21] Appl. No.: 849,546

[22] Filed: Nov. 8, 1977

Related U.S. Application Data

[60] Division of Ser. No. 767,803, Feb. 11, 1977, which is a continuation-in-part of Ser. No. 733,062, Oct. 18, 1976, abandoned.

[51] Int. Cl.$^2$ .......................................... A61K 31/415
[52] U.S. Cl. .................................................. 424/273 R
[58] Field of Search ........................................ 424/273

[56] References Cited

FOREIGN PATENT DOCUMENTS 1135915  9/1962  Fed. Rep. of Germany ...... 424/273 X

Primary Examiner—Frederick E. Waddell
Attorney, Agent, or Firm—Connolly and Hutz

[57] ABSTRACT

A series of spiro-hydantoin compounds has been prepared by condensing the appropriate carbonyl ring compound, such as the corresponding 1-indanone, 1-tetralone, 4-chromanone, thiochroman-4-one, 7,8-dihydroquinolin-5(6H)-one, 6,7-dihydropyrindin-5(5H)-one, thiondane-3-one-1,1-dioxide and 4-oxoisothiochroman-2,2-dioxide, respectively, with potassium cyanide and ammonium carbonate. The resulting hydantoin derivatives are found to be useful in preventing or alleviating chronic diabetic complications. Preferred member compounds include spiro-[imidazolidine-4,1'-indan]-2,5-dione, 6-fluoro-spiro-[chroman-4,4'-imidazolidine]-2',5'-dione, 6-chloro-spiro-[chroman-4,4'-imidazolidine]-2',5'-dione, 6,7-dichloro-spiro-[chroman-4,4'-imidazolidine]-2',5'-dione, 6,8-dichloro-spiro-[chroman-4,4'-imidazolidine]-2',5'-dione, 6'-fluoro-spiro-[imidazolidine-4,4'-thiochroman]-2,5-dione and 6',7'-dichloro-spiro-[imidazolidine-4,4'-thiochroman]-2,5-dione.

7 Claims, No Drawings

HYDANTOIN DERIVATIVES AS THERAPEUTIC AGENTS

CROSS REFERENCE TO RELATED APPLICATIONS

This application is a division of application Ser. No. 767,803 filed Feb. 11, 1977 which is a continuation-in-part of application Ser. No. 733,062 filed Oct. 18, 1976 now abandoned.

BACKGROUND OF THE INVENTION

This invention relates to new and useful hydantoin derivatives in the field of medicinal chemistry. More particularly, it is concerned with a novel series of spiro-hydantoin compounds, which are of especial value in view of their ability to control certain chronic complications arising from diabetes mellitus (e.g., diabetic cataracts and neuropathy). The invention also includes a new method of therapy within its scope.

In the past, various attempts have been made by numerous investigators in the field of organic medicinal chemistry to obtain new and better oral antidiabetic agents. For the most part, these efforts have involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-dioxo-1H-benz[d,e]isoquinoline-2(3H)-acetic acid and some closely-related derivatives thereof are useful for these purposes, even those these particular compounds are not known to be hypoglycemic in nature. These particular aldose reductase inhibitors all function by inhibiting the activity of the enzyme aldose reductase, which is primarily responsible for regulating the reduction of aldoses (like glucose and galactose) to the corresponding polyols (such as sorbitol and galactitol) in the human body. In this way, unwanted accumulations of galactitol in the lens of galactosemic subjects and of sorbitol in the lens, peripheral nervous cord and kidney of various diabetic subjects are thereby prevented or otherwise reduced as the case may be. As a result, these compounds are definitely of value as aldose reductase inhibitors for controlling certain chronic diabetic complications including those of an ocular nature, since it is already known in the art that the presence of polyols in the lens of the eye invariably leads to cataract formation together with a concomitant loss of lens clarity.

SUMMARY OF THE INVENTION

In accordance with the present invention, it has now been rather surprisingly found that various spiro-hydantoin compounds are extremely useful when employed in therapy as aldose reductase inhibitors for the control of certain chronic diabetic complications in a host subject to whom they are administered. More particularly, the novel method of treatment of the present invention involves treating a diabetic host to prevent or alleviate diabetes-associated chronic ocular complications by administering to said host an effective amount of a compound of the formulae:

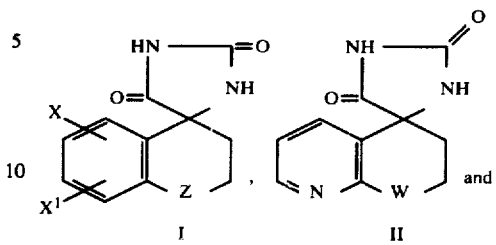

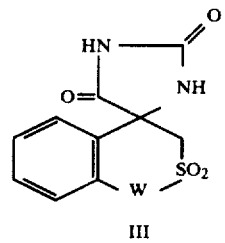

and the base salts thereof with pharmacologically acceptable cations, wherein W is $-(CH_2)_n-$; X is hydrogen and $X^1$ is hydrogen, hydroxy, fluorine, chlorine, lower alkyl or lower alkoxy (each having from one to four carbon atoms); or X and $X^1$, when taken separately, are each chlorine, lower alkyl or lower alkoxy and when taken together are $-OCH_2(CH_2)_nO-$; Y is oxygen or sulfur; Z is W, Y or Q wherein Q is

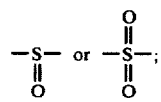

and n is zero or one. These compounds are all potent aldose reductase inhibitors and therefore possess the ability to markedly reduce or even inhibit sorbitol accumulation in the lens and peripheral nerves of various diabetic subjects.

More specifically, the novel compounds of this invention are those of formula I that are disubstituted (X and $X^1$ are each other than hydrogen) and those of formula I that are monosubstituted (X is hydrogen) where Z is $(CH_2)_n$ and n is zero and $X^1$ is other than hydrogen, 4-chlorine and 5-butyl; Z is $(CH_2)_n$ and n is one and $X^1$ is other than hydrogen, 5-methoxy, 6-methoxy or 5-butoxy; Z is oxygen and $X^1$ is other than hydrogen, 6-chlorine, 6-bromine, 8-chlorine, 6-methyl and 6-ethyl, and Z is sulfur and $X^1$ is other than hydrogen. Additionally, those compounds of formula I where Z is Q, as well as those compounds of formulae II-III are also all novel compounds.

Accordingly, the novel compounds of formula I comprise spiro-hydantoin compounds of the formula:

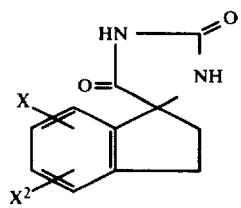

and the base salts thereof with pharmacologically acceptable cations, wherein X is hydrogen and $X^2$ is fluorine, hydroxy or 6'-(lower alkoxy); or X and $X^2$, when taken separately, are each lower alkoxy, and when taken together are —OCH$_2$(CH$_2$)$_n$O—; and n is zero or one.

The novel compounds of formula I also comprise spiro-hydantoins of the formula:

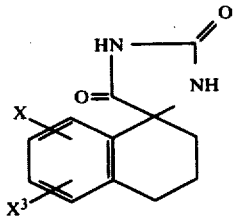

and the base salts thereof with pharmacologically acceptable cations, wherein X is hydrogen and $X^3$ is fluorine, chlorine or bromine; or X and $X^3$, when taken separately, are each chlorine and when taken together are —OCH$_2$(CH$_2$)$_n$O—; and n is zero or one.

The novel compounds of formula I additionally comprise spiro-hydantoins of the formula:

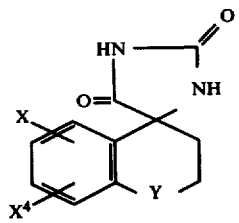

and the base salts thereof with pharmacologically acceptable cations, wherein X is hydrogen and $X^4$ is fluorine, hydroxy or lower alkoxy; or X and $X^4$, when taken separately, are each chlorine or lower alkoxy, and when taken together are —OCH$_2$(CH$_2$)$_n$O—; Y is oxygen or sulfur; and n is zero or one.

Lastly, the novel compounds of formula I also comprise spiro-hydantoin compounds of the formula:

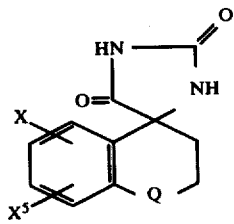

and the base salts thereof with pharmacologically acceptable cations, wherein X is hydrogen and $X^5$ is fluorine, chlorine, bromine or lower alkoxy; or X and $X^5$, when taken separately, are each chlorine or lower alkoxy, and when taken together are —OCH$_2$(CH$_2$)$_n$O—; Q is

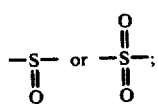

and n is zero or one.

Of especial interest in this connection are such typical and preferred member compounds of the invention as spiro-[imidazolidine-4,1'-indan]-2,5-dione, 6-fluoro-spiro-[chroman-4,4'-imidazolidine]-2',5'-dione, 6-chloro-spiro-[chroman-4,4'-imidazolidine]-2',5'-dione, 6,7-dichloro-spiro-[chroman-4,4'-imidazolidine]-2',5'-dione 6,8-dichloro-spiro-[chroman-4,4'-thiochroman]-2',5'-dione and 6',7'-dichloro-spiro-[imidazolidine-4,4'-thiochroman]-2,5-dione, respectively. These particular compounds are all highly potent as regards their aldose reductase inhibitory activity, in addition to being extremely effective in lowering sorbitol levels in the sciatic nerve and lens of diabetic subjects and galactitol levels in the lens of galactosemic subjects to a remarkably high degree. The preferred 6-fluoro and 6,8-dichloro derivatives are, as previously indicated, new compounds.

DETAILED DESCRIPTION OF THE INVENTION

In accordance with the process employed for preparing the compounds of this invention, an appropriate carbonyl ring compound, such as the corresponding 1-indanone, 1-tetralone, 4-chromanone, thiochroman-4-one, 7,8-dihydroquinolin-5(6H)-one, 6,7-dihydropyrindin-5(5H)-one, thioindane-3-one-1,1-dioxide and 4-oxoisothiochroman-2,2-dioxide of the respective formulae:

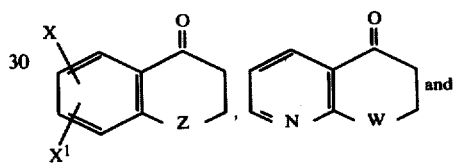

wherein W, X, $X^1$, Y and Z are all as previously defined, is condensed with an alkali metal cyanide (e.g., sodium cyanide or potassium cyanide) and ammonium carbonate to form the desired spiro-hydantoin final product of the structural formulae previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide, etc. In general, the reaction is conducted at a temperature that is in the range of from about 20° C. up to about 120° C. for a period of about two hours to about four days. Although the amount of reactant and reagents employed in the reaction can vary to some extent, it is preferable to employ at least a slight molar excess of the alkali metal cyanide reagent with respect to the carbonyl ring compound starting material in order to effect maximum yield. Upon completion of the reaction, the desired product is easily isolated in a conventional manner, e.g., by first diluting the reaction mixture with water (boiling if necessary) and then cooling the resultant aqueous solution to room temperature, followed by acidification to afford the particular spiro-hydantoin compound in the form of a readily-recoverable precipitate.

Needless to say, compounds of the invention in which Z of formula I is Q and Q is

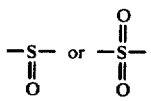

can be prepared from those compounds wherein Z is sulfur by merely oxidizing the latter group of compounds in accordance with standard techniques well known to those skilled in the art. For instance, the use of sodium periodate in this connection leads to the formation of the oxosulfur compounds, while peroxy acids like peracetic acid, perbenzoic acid and m-chloroperoxybenzoic acid, etc., are preferably employed to afford the corresponding dioxosulfur compounds. On the other hand, certain compounds of the invention having a ring substituent (X, $X^1$, etc.) which is halogen (as previously defined) may alternatively be prepared from the corresponding unsubstituted compounds wherein at least one of X and $X^1$ is hydrogen by means of direct halogenation techniques well known to those in the field of synthetic organic chemistry.

The starting materials required for preparing the spiro-hydantoin compounds of this invention are, for the most part, known compounds and are either readily available commercially, like 1-indanone and 6-chloro-4-chromanone, etc., or else they can easily be synthesized by those skilled in the art starting from common chemical reagents and using conventional methods of organic synthesis. For instance, 6-fluoro-4-chromanone is obtained by condensing β-(p-fluorophenoxy)propionic acid in the presence of polyphosphoric acid, while 6,7-dichlorothiochroman-4-one is obtained by condensing β-(3,4-dichlorophenylthio)propionic acid in the presence of concentrated sulfuric acid. In both cases, the starting organic acid is ultimately derived from a commercially available compound.

The chemical bases which are used as reagents in this invention to prepare the aforementioned pharmaceutically acceptable base salts are those which form non-toxic salts with the various herein described acidic spiro-hydantoin compounds, such as 6-fluoro-spiro-[chroman-4,4'-imidazolidine]-2',5'-dione, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned spiro-hydantoin compounds with an aqueous solution of the desired pharmacologically acceptable cation, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents must be employed in order to ensure completeness of reaction and maximum production of yields with respect to the desired final product.

As previously indicated, the spiro-hydantoin compounds of this invention are all readily adapted to therapeutic use as aldose reductase inhibitors for the control of chronic diabetic complications, in view of their ability to reduce lens sorbitol levels in diabetic subjects to a statistically significant degree. For instance, 6-fluoro-spiro-[chroman-4,4'-imidazolidine]-2',5'-dione, a typical and preferred agent of the present invention, has been found to consistently control (i.e., inhibit) the formation of sorbitol levels in diabetic rats to a significantly high degree when given by the oral route of administration at dose levels ranging from 0.75 mg./kg. to 20 mg./kg., respectively, without showing any substantial signs of toxic side effects. The other compounds of this invention also cause similar results. Furthermore, all the herein described compounds of this invention can be administered by either the oral or parenteral routes of administration, for the present purposes at hand, without causing any significant untoward pharmacological side reactions to occur in the subject to whom they are so administered. In general, these compounds are ordinarily administered in dosages ranging from about 0.1 mg. to about 10 mg. per kg. of body weight per day, although variations will necessarily occur depending upon the weight and condition of the subject being treated and the particular route of administration chosen.

In connection with the use of the spiro-hydantoin compounds of this invention for the treatment of diabetic subjects, it is to be noted that these compounds may be administered either alone or in combination with pharmaceutically acceptable carriers by either of the routes previously indicated, and that such administration can be carried out in both single and multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for just such purposes. In general, the therapeutically useful compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or topioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these particular spiro-hydantoins in sesame or peanut oil or in aqueous propylene glycol may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art. Additionally, it is also possible to administer the aforesaid spiro-hydantoin compounds topically via an appropriate opthalmic solution suitable for the present purposes at hand, which can then be given dropwise to the eye.

The activity of the compounds of the present invention, as agents for the control of chronic diabetic complications, is determined by their ability to successfully pass one or more of the following standard biological and/or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

PREPARATION A

A mixture consisting of 3.5 g. (0.019 mole) of $\beta$-(p-fluorophenoxy)propionic acid [Finger et al., *Journal of the American Chemical Society*, Vol. 81, p. 94 (1959)] and 40 g. of polyphosphoric acid was heated on a steam bath for a period of ten minutes and then poured into 300 ml. of ice-water. The resulting aqueous mixture was next extracted with three separate portions of ethyl acetate, and the combined organic layers were subsequently washed with dilute aqueous sodium bicarbonate solution and then with water, followed by drying over anhydrous magnesium sulfate. After removal of the drying agent by means of filtration and the solvent by means of evaporation under reduced pressure, there was ultimately obtained a residue that was subsequently recrystallized from ethanol to afford 2.93 g. (93%) of pure 6-fluoro-4-chromanone, m.p. 114°-116° C.

Anal. Calcd. for $C_9H_7FO_2 \cdot 0.25\ H_2O$: C, 63.34; H, 4.43. Found: C, 63.24; H, 4.15.

PREPARATION B

To a solution of 12.5 g. (0.07 mole) of 3,4-dichlorobenzenethiol (available from the Aldrich Chemical Company, Inc., Milwaukee, Wis.) in 35 ml. of 2N aqueous sodium hydroxide and 5 ml. of ethanol, there was added an ice-cold solution consisting of 7.6 g. (0.07 mole) of $\beta$-chloropropionic acid (also available from Aldrich) and 8.6 g. (0.07 mole) of sodium carbonate monohydrate dissolved in 50 ml. of water. The resulting reaction mixture was then heated on a steam bath for a period of two hours, cooled to room temperature ($\sim$25° C.) and extracted with ethyl acetate to remove any impurities. The saved aqueous portion was then poured into 300 ml. of ice-cold 3N hydrochloric acid and the precipitated solids so obtained were subsequently collected by means of suction filtration. After washing the latter material with water, air-drying to constant weight and recrystallizing from ethyl acetate/n-hexane, there was obtained an 11.4 g. (65%) yield of $\beta$-(3,4-dichlorophenylthio)propionic acid, m.p. 70°-72° C.

Anal. Calcd. for $C_9H_8Cl_2S$: C, 43.04; H, 3.21. Found: C, 43.13; H, 3.25.

A solution of the above product in concentrated sulfuric acid was prepared by adding 5.0 g. (0.02 mole) of $\beta$-(3,4-dichlorophenylthio)propionic acid to 50 ml. of ice-cold concentrated sulfuric acid, with constant agitation being maintained throughout the addition step. The resulting solution was then stirred at 0° C. for a period of 20 minutes and finally at room temperature for another 20 minutes. At this point, the entire reaction mixture was poured into 300 ml. of an ice-water mixture and the precipitated solids were collected by suction filtration, washed with water and air-dried to constant weight. Recrystallization from ethanol then gave 2.5 g. (54%) of pure 6,7-dichlorothiochroman-4-one, m.p. 134°-136° C.

Anal. Calcd. for $C_9H_6Cl_2OS$: C, 46.37; H, 2.60. Found: C, 46.34; H, 2.45.

PREPARATION C

3',4'-Dihydro-spiro-[imidazolidine-4,1'(2'H)-naphthalene]-2,5-dione was prepared according to the procedure described in *Chemical Abstracts*, Vol. 35, p. 65767 (1941), starting from 1-indanone and other readily available materials. The product obtained was identical in every respect with the prior art compound.

EXAMPLE I

A mixture consisting of 13.2 g. (0.1 mole) of 1-indanone (available from the Aldrich Chemical Company, Inc., Milwaukee, Wis.), 9.75 g. (0.15 mole) of potassium cyanide and 28.8 g. (0.3 mole) of powdered ammonium carbonate in 200 ml. of 50% aqueous ethanol was heated in an oil bath at 75° C. for a period of 24 hours. The reaction mixture was then diluted with 800 ml. of water, boiled for 15 minutes and after finally being cooled to room temperature, poured into 600 ml. of ice-cooled, concentrated hydrochloric acid. The resulting crystalline crop, which formed as a precipitate, was subsequently collected by means of suction filtration, washed with water and thereafter recrystallized from methanol-diethyl ether to afford 15.4 g. (76%) of pure spiro-[imidazolidine-4,1'-indan]-2,5-dione, m.p. 238°-240° C. [literature m.p. 239°-240° C., according to Goodson et al., *Journal of Organic Chemistry*, Vol. 25, p. 1920 (1960)].

Anal. Calcd. for $C_{11}H_{10}N_2O_2$: C, 65.33; H, 4.98; N, 13.86. Found: C, 65.28; H, 5.01; N, 13.90.

EXAMPLE II

A mixture consisting of 2.5 g. (0.15 mole) of 6-methoxy-1-indanone (available from the Aldrich Chemical Company, Inc., Milwaukee, Wis.), 1.5 g. (0.23 mole) of potassium cyanide and 6.7 g. (0.07 mole) of ammonium carbonate in 20 ml. of ethanol was placed in a stainless-steel bomb and heated at 110° C. for a period of 20 hours. After cooling to room temperature ($\sim$25° C.), the contents of the bomb were diluted with 100 ml. of water and then acidified to pH 2.0 with 6N hydrochloric acid. The precipitated product so obtained was subsequently collected by means of suction filtration and thereafter recrystallized from ethanol to give 0.49 g. (14%) of pure 6'-methoxy-spiro-[imidazolidine-4,1'-indan]-2,5-dione, m.p. 192°-194° C.

Anal. Calcd. for $C_{12}H_{12}N_2O_3$: C, 62.06; H, 5.21; N, 12.06. Found: C, 61.94; H, 5.26; N, 12.01.

EXAMPLE III

The procedure described in Example II was repeated except that 6-fluoro-1-indanone [*Chemical Abstracts*, Vol. 55, p. 25873a (1961)] was the starting material employed in place of 6-methoxy-1-indanone, using the same molar proportions as before. In this particular case, the corresponding final product obtained was 6'-fluoro-spiro-[imidazolidine-4,1'-indan]-2,5-dione, m.p. 255°-257° C. The yield of pure product was 4.6% of the theoretical value.

Anal. Calcd. for $C_{11}H_{19}FN_2O_2$: C 60.00; H, 4.12; N, 12.72. Found: C, 59.86; H, 4.33; N, 12.49.

EXAMPLE IV

The procedure described in Example II was repeated except that 5,6-dimethoxy-1-indanone [Koo, *Journal of the American Chemical Society*, Vol. 75, p. 1891 (1953)] was the starting material employed in place of 6-methoxy-1-indanone, using the same molar proportions as before. In this particular case, the corresponding final product obtained was 5',6'-dimethoxy-spiro[imidazolidine-4,1'-indan]-2,5-dione, m.p. 246°-248° C. The yield of pure product was 48% of the theoretical value.

Anal. Calcd. for $C_{13}H_{14}N_2O_4$: C, 59.53; H, 5.38; N, 10.68. Found: C, 59.26; H, 5.49; N, 10.54.

EXAMPLE V

The procedure described in Example II was repeated except that 5,6-methylenedioxy-1-indanone [Perkin and Robinson, *Journal of the Chemical Society*, Vol. 91, p. 1084 (1907)] was the starting material employed in place of 6-methoxy-1-indanone, using the same molar proportions as before. In this particular case, the corresponding final product obtained was 5',6'-methylenedioxy-spiro-[imidazolidine-4,1'-indan]-2,5-dione, m.p. 248°-250° C. The yield of pure product was 29% of the theoretical value.

Anal. Calcd. for $C_{12}H_{10}N_2O_4$: C, 58.53; H, 4.09; N, 11.38. Found: C, 58.44; H, 4.14; N, 11.25.

EXAMPLE VI

The procedure described in Example II was repeated except that 5-methoxy-1-indanone (available from the Aldrich Chemical Company, Inc., Milwaukee, Wis.) was the starting material employed in place of 6-methoxy-1-indanone, using the same molar proportions as before. In this particular case, the corresponding final product obtained was 5'-methoxy-spiro-[imidazolidine-4,1'-indan]-2,5-dione, m.p. 167°-169° C. The yield of pure product was 19% of the theoretical value.

Anal. Calcd. for $C_{12}H_{12}N_2O_3$: C, 62.06; H, 5.21; N, 12.06. Found: C, 61.77; H, 5.23; N, 12.14.

EXAMPLE VII

The procedure described in Example II was repeated except that thiochroman-4-one (available from Pfaltz & Bauer, Inc. of Stamford, Conn.) was the starting material employed in place of 6-methoxy-1-indanone, using the same molar proportions as before. In this particular case, the corresponding final product obtained was spiro-[imidazolidine-4,4'-thiochroman]-2,5-dione, m.p. 225°-227° C. (literature m.p. 222°-227° C., according to West German Auslegeschrift No. 1,135,915). The yield of pure product was 44% of the theoretical value.

EXAMPLE VIII

The procedure described in Example II was repeated except that 6-methoxythiochroman-4-one [*Chemical Abstracts*, Vol. 53, p. 7161c (1959)] was the starting material employed in place of 6-methoxy-1-indanone, using the same molar proportions as before. In this particular case, the corresponding final product obtained was 6'-methoxy-spiro-[imidazolidine-4,4'-thiochroman]-2,5-dione, m.p. 170°-172° C. The yield of pure product was 41% of the theoretical value.

Anal. Calcd. for $C_{12}H_{12}N_2O_3S$: C, 54.53; H, 4.58; N, 10.61. Found: C, 54.64; H, 4.67; N, 10.66.

EXAMPLE IX

The procedure described in Example II was repeated except that 6-chlorothiochroman-4-one [*Chemical Abstracts*, Vol. 55, p. 12397c (1961)] was the starting material employed in place of 6-methoxy-1-indanone, using the same molar proportions as before. In this particular case, the corresponding final product obtained was 6'-chloro-spiro-[imidazolidine-4,4'-thiochroman]-2,5-dione, m.p. 244°-246° C. The yield of pure product was 53% of the theoretical value.

Anal. Calcd. for $C_{11}H_9ClN_2O_2S$: C, 49.16; H, 3.38; N, 10.43. Found: C, 49.23; H, 3.40; N, 10.39.

EXAMPLE X

The procedure described in Example II was repeated except that 6-bromothiochroman-4-one [Arndt, *Chemische Berichte*, Vol. 58, p. 1612 (1925)] was the starting material employed in place of 6-methoxy-1-indanone, using the same molar proportions as before. In this particular case, the corresponding final product obtained was 6-bromo-spiro-[imidazolidine-4,4'-thiochroman]-2,5-dione, m.p. 234°-236° C. The yield of pure product was 56% of the theoretical value.

Anal. Calcd. for $C_{11}H_9BrN_2O_2S$: C, 42.18; H, 2.90; N, 8.95. Found: C, 41.98; H, 2.92; N, 8.95.

EXAMPLE XI

The procedure described in Example II was repeated except that 6,7-dichlorothiochroman-4-one (prepared as described in Preparation B) was the starting material employed in place of 6-methoxy-1-indanone, using the same molar proportions as before. In this particular case, the corresponding final product obtained was 6',7'-dichloro-spiro-[imidazolidine-4,4'-thiochroman]-2,5-dione, m.p. 298°-300° C. The yield of pure product was 49% of the theoretical value.

Anal. Calcd. for $C_{11}H_8Cl_2N_2O_2S$: C, 43.58; H, 2.66; N, 9.24. Found: C, 43.77; H, 2.85; N, 9.38.

EXAMPLE XII

The procedure described in Example II was repeated except that 6-fluorothiochroman-4-one [*Chemical Abstracts*, Vol. 70, p. 47335x (1969)] was the starting material employed in place of 6-methoxy-1-indanone, using the same molar proportions as before. In this particular case, the corresponding final product obtained was 6'-fluoro-spiro-[imidazolidine-4,4'-thiochroman]-2,5- dione, m.p. 200°–202° C. The yield of pure product was 60% of the theoretical value.

Anal. Calcd. for $C_{11}H_9FN_2O_2S$: C, 52.37; H, 3.60; N, 11.11. Found: C, 52.36; H, 3.73; N, 11.05.

EXAMPLE XIII

The procedure described in Example II was repeated except that 8-chlorothiochroman-4-one [*Chemical Abstracts*, Vol. 53, p. 7161c (1959)] was the starting material employed in place of 6-methoxy-1-indanone, using the same molar proportions as before. In this particular case, the corresponding final product obtained was 8'-chloro-spiro-[imidazolidine-4,4'-thiochroman]-2,5-dione, m.p. 265°–267° C. The yield of pure product was 66% of the theoretical value.

Anal. Calcd. for $C_{11}H_9ClN_2O_2S$: C, 49.16; H, 3.38; N, 10.43. Found: C, 49.32; H, 3.50; N, 10.38.

EXAMPLE XIV

The procedure described in Example II was repeated except that 7-chlorothiochroman-4-one [*Chemical Abstracts*, Vol. 52, p. 11044b (1958)] was the starting material employed in place of 6-methoxy-1indanone, using the same molar proportions as before. In this particular case, the corresponding final product obtained was 7'-chloro-spiro-[imidazolidine-4,4'-thiochroman]-2,5-dione, m.p. 235°–237° C. The yield of pure product was 67% of the theoretical value.

Anal. Calcd. for $C_{11}H_9ClN_2O_3S$: C, 49.16; H, 3.38; N, 10.43. Found: C, 49.32; H, 3.36; N, 10.03.

EXAMPLE XV

The procedure described in Example II was repeated except that 7,8-dihydroquinolin-5(6H)-one (available from the Aldrich Chemical Company, Inc., Milwaukee, Wis.) was the starting material employed in place of 6-methoxy-1-indanone, using the same molar proportions as before. In this particular case, the corresponding final product obtained was 7',8'-dihydro-spiro-[imidazolidine-4,5'(6H)-quinoline]-2,5-dione, m.p. 275°–277° C. The yield of pure product was 39% of the theoretical value.

Anal. Calcd. for $C_{11}H_{11}N_3O_2$: C, 60.82; H, 5.10; N, 19.35. Found: C, 60.41; H, 5.28; N, 19.29.

EXAMPLE XVI

The procedure described in Example II was repeated except that 7-methoxy-1-tetralone (available from the Aldrich Chemical Company, Inc., Milwaukee, Wis.) was the starting material employed in place of 6-methoxy-1-indanone, using the same molar proportions as before. In this particular case, the corresponding final product obtained was 3',4'-dihydro-7'-methoxy-spiro-[imidazolidine-4,1'(2'H)naphthalene]-2,5-dione, m.p. 227°–229° C. The yield of pure product was 59% of the theoretical value.

Anal. Calcd. for $C_{13}H_{14}N_2O_3$: C, 63.40; H, 5.73; N, 11.38. Found: C, 63.19; H, 5.68; N, 11.30.

EXAMPLE XVII

The procedure described in Example II was repeated except that 6,7-dimethoxytetralone [Howell and Taylor, *Journal of the Chemical Society*, p. 1248 (1958)] was the starting material employed in place of 6-methoxy-1-indanone, using the same molar proportions as before. In this particular case, the corresponding final product obtained was 3',4'-dihydro-6',7'-dimethoxy-spiro-[imidazolidine-4,1'(2H)naphthalene]-2,5-dione, m.p. 238°–240° C. The yield of pure product was 49% of the theoretical value.

Anal. Calcd. for $C_{14}H_{16}N_2O_4$: C, 60.86; H, 5.84; N, 10.14. Found: C, 60.94; H, 6.04; N, 10.48.

EXAMPLE XVIII

The procedure described in Example II was repeated except that 6-methoxy-1-tetralone (available from the Aldrich Chemical Company, Inc., Milwaukee, Wis.) was the starting material employed in place of 6-methoxy-1-indanone, using the same molar proportions as before. In this particular case, the corresponding final product obtained was 3',4'-dihydro-6'-methoxy-spiro-[imidazolidine-4,1'(2'H)naphthalene]-2,5-dione, m.p. 219°–221° C. (literature m.p. 219°–220° C., according to U.S. Pat. No. 3,532,744)

EXAMPLE XIX

A solution of 1.18 g. (0.005 mole) of 6'-methoxy-spiro-[imidazolidine-4,1'-indan]-2,5-dione (prepared as described in Example II) in 10 ml. of methylene chloride was cooled to −65° C. and there was subsequently added thereto, in a dropwise manner, a solution consisting of 1.44 ml. (0.015 mole) of boron tribromide dissolved in 10 ml. of methylene chloride, while stirring the entire reaction mixture under a nitrogen atmosphere. The resulting mixture was then allowed to attain room temperature (∼25° C.) via removal of the cooling bath and thereafter kept at that point for a period of seven hours. Upon completing this step, 30 ml. of water were added to the mixture in a dropwise manner and the separated organic layer was subsequently collected and dried over anhydrous magnesium sulfate. After removal of the organic solvent (i.e., methylene chloride) by means of evaporation under reduced pressure, there was ultimately obtained a residual material that was subsequently recrystallized from ethanol to give 240 mg. (22%) of pure 6'-hydroxy-spiro-[imidazolidine-4,1'-indan]-2,5-dione, m.p. 253°–255° C.

Anal. Calcd. for $C_{11}H_{10}N_2O_3$: C, 60.54; H, 4.62; N, 12.84. Found: C, 60.29; H, 4.66; N, 12.93.

EXAMPLE XX

A mixture consisting of 5.0 g. (0.033 mole) of 4-chromanone (available from the Aldrich Chemical Company, Inc., Milwaukee, Wis.), 2.8 g. (0.043 mole) of potassium cyanide and 8.26 g. (0.086 mole) of powdered ammonium carbonate in 40 ml. of ethanol was placed in a stainless-steel bomb and heated to 60° C. in an oil bath for a period of 24 hours. The reaction mixture was then diluted with 300 ml. of water, boiled for 15 minutes and after finally being cooled to room temperature, acidified with 6N hydrochloric acid. The precipitated product so obtained was then collected by means of suction filtration and subsequently recrystallized from ethanol to give 2.5 g. (35%) of pure spiro-[chroman-4,4'-imidazolidine]-2',5'-dione, m.p. 236°–238° C. (literature m.p. 236°–242° C., according to West German Auslegeschrift No. 1,135,915).

Anal. Calcd. for $C_{11}H_{11}NO_3$: C, 64.38; H, 5.40; N, 6.83. Found: C, 64.18; H, 5.38; N, 6.83.

EXAMPLE XXI

The procedure described in Example XX was repeated except that 6-methoxy-4-chromanone (British Pat. No. 1,024,645) was the starting material employed in place of 4-chromanone, using the same molar proportions as before. In this particular case, the corresponding final product obtained was 6-methoxy-spiro-[chroman-4,4'-imidazolidine]-2',5'-dione, m.p. 170°–172° C. The yield of pure product was 32% of the theoretical value.

Anal. Calcd. for $C_{12}H_{12}N_2O_4$: C, 58.06; H, 4.87; N, 11.29. Found: C, 58.04; H, 4.98; N, 11.17.

EXAMPLE XXII

The procedure described in Example XX was repeated except that 6-fluoro-4-chromanone (prepared as described in Preparation A) was the starting material employed in place of 4-chromanone, using the same molar proportions as before. In this particular case, the corresponding final product obtained was 6-fluoro-spiro-[chroman-4,4'-imidazolidine]-2',5'-dione, m.p. 239°–241° C. The yield of pure product was 36% of the theoretical value.

Anal. Calcd. for $C_{11}H_9FN_2O_3$: C, 55.93; H, 3.84; N, 11.86. Found: C, 55.54; H, 3.88; N, 12.12.

EXAMPLE XXIII

The procedure described in Example XX was repeated except that 6,7-dichloro-4-chromanone (West German Offenlegungschrift No. 1,928,027) was the starting material employed in place of 4-chromanone, using the same molar proportions as before. In this particular case, the corresponding final product obtained was 6,7-dichloro-spiro-[chroman-4,4'-imidazolidine]-2',5'-dione, m.p. 263°–265° C. The yield of pure product was 8% of the theoretical value.

Anal. Calcd. for $C_{11}H_8Cl_2N_2O_3$: C, 46.02; H, 2.81; N, 9.76. Found: C, 45.83; H, 2.94; N, 9.65.

EXAMPLE XXIV

The procedure described in Example XX was repeated except that 6,8-dichloro-4-chromanone [Huckle et al., Journal of Medicinal Chemistry, Vol. 12, p. 277 (1969)] was the starting material employed in place of 4-chromanone, using the same molar proportions as before. In this particular case, the corresponding final product obtained was 6,8-dichloro-spiro-[chroman-4,4'-imidazolidine]-2',5'-dione, m.p. 234°–235° C. The yield of pure product was 20% of the theoretical value.

Anal. Calcd. for $C_{11}H_8Cl_2N_2O_3$: C, 46.02; H, 2.81; N, 9.76. Found: C, 45.81; H, 2.74; N, 9.69.

EXAMPLE XXV

A mixture consisting of 4.57 g. (0.025 mole) of 6-chloro-4-chromanone (available from the Aldrich Chemical Company, Inc., Milwaukee, Wis.), 2.8 g. (0.043 mole) of potassium cyanide and 9.6 g. (0.1 mole) of powdered ammonium carbonate in 62.5 ml. of 50% aqueous ethanol was heated to 60° C. for a period of 48 hours. The reaction mixture was then cooled to room temperature (~25° C.), diluted with 300 ml. of water and thereafter acidified with 6N hydrochloric acid. The precipitated solids so obtained were subsequently collected by means of suction filtration and thereafter recrystallized from ethanol to yield 5.1 g. (81%) of pure 6-chloro-spiro-[chroman-4,4'-imidazolidine]-2',5'-dione, m.p. 268°–270° C. (literature m.p. 267°–270° C., according to West German Auslegeschrift No. 1,135,915).

Anal. Calcd. for $C_{11}H_9ClN_2O_3$: C, 52.29; H, 3.59; N, 11.09. Found: C, 52.15; H, 3.73; N, 10.99.

EXAMPLE XXVI

The procedure described in Example XXV was repeated except that 5-methoxy-1-tetralone (available from the Aldrich Chemical Company, Inc., Milwaukee, Wis.) was the starting material employed in place of 6-chloro-4-chromanone, using the same molar proportions as before. In this particular case, the corresponding final product obtained was 3',4'-dihydro-5'-methoxy-spiro-[imidazolidine-4,1'(2'H)-naphthalene]-2,5-dione, m.p. 243'–243.5° C. [literature m.p. 242°–242.5° C., according to Sarges et al., Journal of Medicinal Chemistry, Vol. 16, p. 1003 (1973)].

Anal. Calcd. for $C_{13}H_{14}N_2O_3$: C, 63.40; H, 5.73; N, 11.38. Found: C, 63.10; H, 5.70; N, 11.47.

EXAMPLE XXVII

The procedure described in Example XXV was repeated except that 8-chloro-4-chromanone [Chemical Abstracts, Vol. 34, p. 4735$^8$ (1940)] was the starting material employed in place of 6-chloro-4-chromanone, using the same molar proportions as before. In this particular case, the corresponding final product obtained was 8-chloro-spiro-[chroman-4,4'-imidazolidine]-2',5'-dione, m.p. 231°–233° C. (literature m.p. 231°–235° C., according to West German Auslegeschrift No. 1,135,915). The yield of pure product was 34% of the theoretical value.

Anal. Calcd. for $C_{11}H_9ClN_2O_3$: C, 52.29; H, 3.59; N, 11.09. Found: C, 52.21; H, 3,74; N, 11.12.

EXAMPLE XXVIII

The procedure described in Example XXV was repeated except that 6-bromo-4-chromanone [Gilman et al., Journal of the American Chemical Society, Vol. 73, p. 4205 (1951)] was the starting material employed in place of 6-chloro-4-chromanone, using the same molar proportions as before and the reaction temperature was 55° C. instead of 60° C. In this particular case, the corresponding final product obtained was 6-bromo-spiro-[chroman-4,4'-imidazolidine]-2',5'-dione, m.p. 266°–268° C. (literature m.p. 264°–269° C., according to West German Auslegeschrfit No. 1,135,915). The yield of pure product was 15% of the theoretical value.

EXAMPLE XXIX

To a solution of 1.09 g. (0.005 mole) of spiro-[chroman-4,4'-imidazolidine]-2',5'-dione (prepared as described in Example XX) and 10 mg. of ferric chloride in 6 ml. of dry methylformamide cooled to −40° C., there was added in a dropwise manner and with constant agitation a solution consisting of 355 mg. of chlorine gas dissolved in 4 ml. of dry dimethylformamide. The resulting reaction mixture was then maintained at −40° C. for a period of 30 minutes (with stirring) before being allowed to attain room temperature (~25° C.). After being kept at the latter point for a period of 2.5 hours, it was poured into 250 ml. of ice-cold water to afford a crystalline precipitate that was subsequently collected by means of suction filtration and then air-dried to constant weight. Recrystallization of the latter material from glacial acetic acid (6 ml.) then gave 0.31 g. (25%) of pure 6-chloro-spiro-[chroman-4,4'-imidazolidine]-2',5'-dione that was identical in every respect with the product of Example XXV.

EXAMPLE XXX

A mixture consisting of 252 mg. (0.001 mole) of 6'-fluoro-spiro-[imidazolidine-4,4'-thiochroman]-2,5-dione (prepared as described in Example XII) in 10 ml. of methylene chloride, together with 50 mg. of a 40% aqueous solution of tetrabutylammonium hydroxide and 224 mg. (0.01 mole) of sodium periodate in 5 ml. of water was stirred at room temperature (~25° C.) for a period of one hour. The precipitated solids so obtained wrere subsequently collected by means of suction filtration and thereafter recrystallized from ethanol (3 ml.) to yield 60 mg. (22%) of pure 6'-fluoro-spiro-[imidazolidine-4,4'-thiochroman]-2,5-dione-1'-oxide, m.p. 289°-291° C.

Anal. Calcd. for $C_{11}H_9FN_2O_3S$: C, 49.25; H, 3.38; N, 10.44. Found: C 49.27; H, 3.35; N, 10.35.

EXAMPLE XXXI

To a suspension of 0.595 g. (0.00236 mole) of 6'-fluoro-spiro-[imidazolidine-4,4'-thiochroman]-2,5-dione (prepared as described in Example XII) in 50 ml. of chloroform contained in a 250 ml. three-necked round-bottomed reaction flask, there was added in small portions over a one-hour period 1.00 g. (0.00579 mole) of m-chloroperoxybenzoic acid. The resulting slurry was then stirred at room temperature (~25° C.) for a period of 36 hours and finally diluted with 500 ml. of ethyl acetate. The yellow organic layer so obtained was next washed with four-50ml. portions of saturated aqueous sodium bicarbonate solution, dried over anhydrous magnesium sulfate, filtered and the solvent portion then removed in vacuo to afford 0.50 g. (74.5%) of crude 6'-fluoro-spiro-[imidazolidine-4,4'-thiochroman]-2,5-dione-1',1'-dioxide in the form of a white crystalline residue. Recrystallization from ethanol/ethyl acetate/n-hexane then gave the pure material (m.p. 179°-180° C. with decomp.) as a first crop of fine white crystals (yield, 0.295 g.). Two additional recrystallizations from ethanol/ethyl acetate raised the melting point of the analytical sample to 184°-186° C. (decomp.).

Anal. Calcd. for $C_{11}H_9FN_2O_4S.0.5CH_3COOC_2H_5$: C, 47.55; H, 3.99: N, 8.53. Found: C, 47.54; H, 3.93; N, 8.56.

EXAMPLE XXXII

The procedure described in Example XXXI was repeated except that 0.234 g. (0.001 mole) of spiro-[imidazolidine-4,4'-thiochroman]-2,5-dione (prepared as described in Example VII) and 0.426 g. (0.00247 mole) of m-chloro-peroxybenzoic acid were reacted together to afford 0.20 g. (75%) of pure spiro-[imidazolidine-4,4'-thiochroman]-2,5-dione-1',1'-dioxide. Recrystallization from methanol/ethanol/n-hexane then gave the analytical sample (m.p. 280°-281° C.).

Anal. Calcd. for $C_{11}H_{10}N_2O_4S$: C, 49.61; H, 3.78; N, 10.52. Found: C, 49.82; H, 3.85; N, 10.19.

EXAMPLE XXXIII

A mixture consisting of 1.0 g. (0.00549 mole) of thi-oindane-3-one-1,1-dioxide [Regitz, *Chemische Berichte,* Vol. 98, p. 36 (1965)], 0.613 g. (0.0094 mole) of potassium cyanide and 21.9 g. (0.021 mole) of ammonium carbonate in 14 ml. of 50% aqueous ethanol was placed in a 50 ml. round-bottomed reaction flask and heated at 60° C. for a period of 48 hours while under a nitrogen atmosphere. The reaction mixture was then diluted with 70 ml. of water, a trace of solid was removed by means of filtration and the filtrate was subsequently acidified with 6N hydrochloric acid. The precipitated product obtained in this manner was thereafter recovered by filtration, redissolved in 4N aqueous potassium hydroxide and finally reacidified with 6N hyrochloric acid. The acidified solution containing the product was saturated with sodium chloride and then extracted with six-150 ml. portions of fresh ethyl acetate, with the resulting organic layers subsequently being combined and dried over anhydrous magnesium sulfate. Upon removal of the drying agent by means of filtration and the organic solvent by means of evaporation under reduced pressure, there was obtained 0.50 g. (36%) of pure spiro-[imidazolidine-3,3'-thioindan]-2,5-dione, m.p. 287° C. (decomp.) after two recrystallizations from ethanol/ethyl acetate/n-hexane.

Anal. Calcd. for $C_{10}H_8N_2O_4S$: C, 47.61; H, 3.20; N, 11.11. Found: C, 47.77; H, 3.28; N, 10.85.

EXAMPLE XXXIV

A mixture consisting of 2.75 g. (0.01562 mole) of 6,8-dimethyl-4-chromanone [*Chemical Abstracts,* Vol. 58, p. 13900c (1964)], 3.5 g. (0.0538 mole) of potassium cyanide and 10.5 g. (0.109 mole) of ammonium carbonate in 60 ml. of 50% aqueous ethanol was placed in a 125 ml. round-bottomed reaction flask and heated via an oil bath at 65° C. for a period of 48 hours while under a nitrogen atmosphere. The reaction mixture was then cooled to room temperature (~25° C.) and filtered and the resulting filtrate subsequently extracted with 50 ml. of diethyl ether. The resulting aqueous layer was then saved and subsequently acidified to pH 2.0 with 3N hydrochloric acid (cooling was necessary). The cloudy mixture so obtained was next extracted with three-200 ml. portions of ethyl acetate and the combined organic layers were thereafter re-extracted with three-50 ml. portions of 4N aqueous potassium hydroxide. The combined basic aqueous layers were reacidified again to pH 2.0 with 3N hydrochloric acid in the same manner as before and then saturated with sodium chloride prior to extraction with three-200 ml. portions of fresh ethyl acetate. The combined organic layers were subsequently dried over an anhydrous magnesium sulfate and filtered. Upon removal of the solvent from the filtrate by means of evaporation under reduced pressure, there was ultimately obtained 2.50 g. (65%) of 6,8-dimethyl-spiro-[chroman-4,4'-imidazolidine]-2',5'-dione, m.p. 185°-190° C. (decomp.). Two recrystallizations from aqueous ethanol then gave analytically pure material (m.p. 188°-189° C.).

Anal. Calcd. for $C_{13}H_{14}N_2O_3$: C, 63.40; H, 5.73; N, 11.38. Found: C, 63.05; H, 5.69; N, 11.33.

EXAMPLE XXXV

The following spiro-hydantoin compounds are prepared by employing the procedures described in the previous examples, starting from readily available materials in each instance:

6'-chloro-spiro-[imidazolidine-4,1'-indan]-2,5-dione
6'-bromo-spiro-[imidazolidine-4,1'-indan]-2,5-dione
5'-fluoro-spiro-[imidazolidine-4,1'-indan]-2,5-dione
5'-methyl-spiro-[imidazolidine-4',1-indan]-2,5-dione
6'-(n-butyl)-spiro-[imidazolidine-4',1-indan]-2,5-dione
5'-hydroxy-spiro-[imidazolidine-4,1'-indan]-2,5-dione
6'-ethoxy-spiro-[imidazolidine-4,1'-indan]-2,5-dione
5'-(n-butoxy)-spiro-[imidazolidine-4,1'-indan]-2,5-dione
5',6'-dichloro-spiro-[imidazolidine-4,1'-indan]-2,5-dione
5',6'-dimethyl-spiro-[imidazolidine-4',1-indan]-2,5-dione
5',6'-di(n-propyl)-spiro-[imidazolidine-4',1-indan]-2,5-dione
5',6'-di(n-propoxy)-spiro-[imidazolidine-4,1'-indan]-2,5-dione
5',6'-ethylenedioxy-spiro-[imidazolidine-4,1'-indan]-2,5-dione 8-bromo-spiro-[chroman-4,4'-imidazolidine]-2',5'-dione
6-(n-butyl)-spiro-[chroman-4,4'-imidazolidine]-2',5'-dione
7-methyl-spiro-[chroman-4,4'-imidazolidine]-2',5'-dione
6-hydroxy-spiro-[chroman-4,4'-imidazolidine]-2',5'-dione
6-ethoxy-spiro-[chroman-4,4'-imidazolidine]-2',5'-dione
6-(n-butoxy)-spiro-[chroman-4,4'-imidazolidine-2',5'-dione
7-isopropoxy-spiro-[chroman-4,4'-imidazolidine]-2',5'-dione
6,8-di(n-butyl)-spiro-[chroman-4,4'-imidazolidine]-2',5'-dione
6,7-dimethoxy-spiro-[chroman-4,4'-imidazolidine]-2',5'-dione
6,8-di(n-butoxy)-spiro-[chroman-4,4'-imidazolidine]-2',5'-dione
6,7-ethylenedioxy-spiro-[chroman-4,4'-imidazolidine]-2',5'-dione
8'-fluoro-spiro-[imidazolidine-4,4'-thiochroman]-2,5-dione
7'-bromo-spiro-[imidazolidine-4,4'-thiochroman]-2,5-dione
6'-hydroxy-spiro-[imidazolidine-4,4'-thiochroman]-2,5-dione
6'-methyl-spiro-[imidazolidine-4,4'-thiochroman]-2,5-dione
7'-(n-butyl)-spiro-[imidazolidine-4,4'-thiochroman]-2,5-dione
7'-(n-butoxy)-spiro-[imidazolidine-4,4'-thiochroman]-2,5-dione
6'-isopropoxy-spiro-[imidazolidine-4,4'-thiochroman]-2,5-dione
6',8'-dichloro-spiro-[imidazolidine-4,4'-thiochroman]-2,5-dione
6',7'-dimethyl-spiro-[imidazolidine-4,4'-thiochroman]-2,5-dione
6',8'-di(n-butyl)-spiro-[imidazolidine-4,4'-thiochroman]-2,5-dione
6',7'-dimethoxy-spiro-[imidazolidine-4,4'-thiochroman]-2,5-dione
6',7'-diethoxy-spiro-[imidazolidine-4,4'-thiochroman]-2,5-dione
6',8'-di(n-butoxy)-spiro-[imidazolidine-4,4'-thiochroman]-2,5-dione
6',7'-methylenedioxy-spiro-[imidazolidine-4,4'-thiochroman]2,5-dione
6',7'-ethylenedioxy-spiro-[imidazolidine-4,4'-thiochroman]-2,5-dione
spiro-[imidazolidine-4,4'-thiochroman]-2,5-dione-1'-oxide
8'-chloro-spiro-[imidazolidine-4,4'-thiochroman]-2,5-dione-1'-oxide
6'-bromo-spiro-[imidazolidine-4,4'-thiochroman]-2,5-dione-1'-oxide
6'-methyl-spiro-[imidazolidine-4,4'-thiochroman]-2,5-dione-1'-oxide
7'-(n-butyl)-spiro-[imidazolidine-4,4'-thiochroman]-2,5-dione-1'-oxide
6'-methoxy-spiro-[imidazolidine-4,4'-thiochroman]-2,5-dione-1'-oxide
7'-(n-butoxy)-spiro-[imidazolidine-4,4'-thiochroman]-2,5-dione-1'-oxide
6',7'-dichloro-spiro-[imidazolidine-4,4'-thiochroman]-2,5-dione-1'-oxide
6',7'-dimethyl-spiro-[imidazolidine-4,4'-thiochroman]-2,5-dione-1'-oxide
6',8'-di(n-butyl)-spiro-[imidazolidine-4,4'-thiochroman]-2,5-dione-1'-oxide
6',7'-dimethoxy-spiro-[imidazolidine-4,4'-thiochroman]-2,5-dione-1'-oxide
6',7'-diethoxy-spiro-[imidazolidine-4,4'-thiochroman]-2,5-dione-1'-oxide
6',8'-di(n-butoxy)-spiro-[imidazolidine-4,4'-thiochroman]-2,5-dione-1'-oxide
6',7'-methylenedioxy-spiro-[imidazolidine-4,4'-thiochroman]-2,5-dione-1'-oxide
6',7'-ethylenedioxy-spiro-[imidazolidine-4,4'-thiochroman]-2,5-dione-1'-oxide
8'-chloro-spiro-[imidazolidine-4,4'-thiochroman]-2,5-dione-1',1'-dioxide
6'-methyl-spiro-[imidazolidine-4,4'-thiochroman]-2,5-dione-1',1'-dioxide
7'-(n-butyl)-spiro-[imidazolidine-4,4'-thiochroman]-2,5-dione-1',1'-dioxide
6'-methoxy-spiro-[imidazolidine-4,4'-thiochroman]-2,5-dione-1',1'-dioxide
7'-(n-butoxy)-spiro-[imidazolidine-4,4'-thiochroman]-2,5-dione-1',1'-dioxide
6',7'-dichloro-spiro-[imidazolidine-4,4'-thiochroman]-2,5-dione-1',1'-dioxide
6',7'-dimethyl-spiro-[imidazolidine-4,4'-thiochroman]-2,5-dione-1',1'-dioxide
6',7'-dimethoxy-spiro-[imidazolidine-4,4'-thiochroman]-2,5-dione-1',1'-dioxide
6',7'-diethoxy-spiro-[imidazolidine-4,4'-thiochroman]-2,5-dione-1',1'-dioxide
6',8'-di(n-butoxy)-spiro-[imidazolidine-4,4'-thiochroman]-2,5-dione-1',1'-dioxide
6',7'-methylenedioxy-spiro-[imidazolidine-4,4'-thiochroman]-2,5-dione-1',1'-dioxide
6',7'-ethylenedioxy-spiro-[imidazolidine-4,4'-thiochroman]-2,5-dione-1',1'-dioxide
spiro-[imidazolidine-4,4'-isothiochroman]-2,5-dione-1',1'-dioxide
3',4'-dihydro-7'-fluoro-spiro-[imidazolidine-4,1'-(2'H)-naphthalene]-2,5-dione
3',4'-dihydro-7'-chloro-spiro-[imidazolidine-4,1'(2'H)-naphthalene]-2,5-dione
3',4'-dihydro-6'-bromo-spiro-[imidazolidine-4,1'(2'H)-naphthalene]-2,5-dione
3',4'-dihydro-5'-isopropyl-spiro-[imidazolidine-4,1'-(2'H)-naphthalene]-2,5-dione
3',4'-dihydro-6'-methyl-spiro-[imidazolidine-4,1'(2'H)-naphthalene]-2,5-dione
3',4'-dihydro-7'-(n-butyl)-spiro-[imidazolidine-4,1'(2'H)-naphthalene]-2,5-dione
3',4'-dihydro-5'-hydroxy-spiro-[imidazolidine-4,1'(2'H)-naphthalene]-2,5-dione
3',4'-dihydro-5'-ethoxy-spiro-[imidazolidine-4,1'(2'H)-naphthalene]-2,5-dione
3',4'-dihydro-7'-(n-butoxy)-spiro-[imidazolidine-4,1'(2'H)-naphthalene]-2,5-dione
3',4'-dihydro-6',7'-dichloro-spiro-[imidazolidine-4,1'(2'H)-naphthalene]-2,5-dione
3',4'-dihydro-6',7'-diethyl-spiro-[imidazolidine-4,1'(2'H)-naphthalene]-2,5-dione
3',4'-dihydro-6',7'-dimethoxy-spiro-[imidazolidine-4,1'(2'H)-naphthalene]-2,5-dione
3',4'-dihydro-6,7-di(n-propoxy)-spiro-[imidazolidine-4,1'(2'H)-naphthalene]-2,5-dione
3',4'-dihydro-6',7'-methylenedioxy-spiro-[imidazolidine-4,1'(2'H)-naphthalene]-2,5-dione
3',4'-dihydro-6',7'-ethylenedioxy-spiro-[imidazolidine-4,1'(2'H)-naphthalene]-2,5-dione 6',7'-dihydro-spiro-[imidazolidine-4,5'(5H)-pyrindine]-2,5-dione

EXAMPLE XXXVI

The sodium salt of 6-fluoro-spiro-[chroman-4,4'-imidazolidine]-2',5'-dione is prepared by dissolving said compound in water containing an equivalent amount in moles of sodium hydroxide and then freeze-drying the mixture. In this way, the desired alkali metal salt of the hydantoin is obtained in the form of an amorphous powder which is freely soluble in water.

In like manner, the potassium and lithium salts are also similarly prepared, as are the alkali metal salts of all the other spiro-hydantoin compounds of this invention which are reported in Examples I-XXI and XXIII-XXXV, respectively.

EXAMPLE XXXVII

The calcium salt of 6-fluoro-spiro-[chroman-4,4'-imidazolidine]-2',5'-dione is prepared by dissolving said compound in water containing an equivalent amount in moles of calcium hydroxide and then freeze-drying the mixture. The corresponding magnesium salt is also prepared in this manner, as are all the other alkaline-earth metal salts not only of this particular compound, but also of those spiro-hydrantoins previously described in Examples I-XXI and XXIII-XXXV, respectively.

EAMPLE XXXVIII

A dry solid pharmaceutical composition is prepared by blending the following materials together in the proportions by weight specified below:

| | |
|---|---|
| 6-Fluoro-spiro-[chroman-4,4'-imidazolidine]-2',5'-dione | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg. of the active ingredient. Other tablets are also prepared in a similar fashion containing 25, 50 and 100 mg. of the active ingredient, respectively, by merely using the appropriate amount of the hydantoin compound in each case.

EXAMPLE XXXIX

A dry solid pharmaceutical composition is prepared by combining the following materials together in the proportions by weight indicated:

| | |
|---|---|
| 6-Chloro-spiro-[chroman-4,4'-imidazolidine]-2',5'-dione | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE XL

The following spiro-hydantoin compounds of Preparation C and Examples I-XXVIII and XXX-XXXIV, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from calf lens. The results obtained with each compound are expressed below in terms of percent inhibition of enzyme activity with respect to the various concentration levels tested:

| Compound | Percent Inhibition (%) | | | |
|---|---|---|---|---|
| | $10^{-4}$M | $10^{-5}$M | $10^{-6}$M | $10^{-7}$M |
| Prod. of Prep. C | 72 | 34 | 13 | 7 |
| Prod. of Ex. I | 73 | 39 | 18 | −11 |
| Prod. of Ex. II | 97 | 61 | 17 | 1 |
| Prod. of Ex. III | 74 | 12 | 22 | −1 |
| Prod. of Ex. IV | 90 | 81 | 35 | 9 |
| Prod. of Ex. V | 92 | 67 | 25 | 3 |
| Prod. of Ex. VI | 82 | 60 | 13 | −10 |
| Prod. of Ex. VII | 92 | 64 | 10 | −5 |
| Prod. of Ex. VIII | 76 | 60 | 18 | 7 |
| Prod. of Ex. IX | 79 | 87 | 71 | 30 |
| Prod. of Ex. X | 32 | — | — | — |
| Prod. of Ex. XI | 67 | 84 | 76 | 69 |
| Prod. of Ex. XII | 81 | 77 | 66 | 38 |
| Prod. of Ex. XIII | 60 | — | — | — |
| Prod. of Ex. XIV | 70 | — | — | — |
| Prod. of Ex. XV | 83 | 54 | 9 | −2 |
| Prod. of Ex. XVI | 54 | — | 23 | — |
| Prod. of Ex. XVII | 82 | 26 | 8 | 16 |
| Prod. of Ex. XVIII | 72 | 38 | 15 | 7 |
| Prod. of Ex. XIX | 93 | 31 | 11 | −30 |
| Prod. of Ex. XX | 73 | 64 | −9 | −16 |
| Prod. of Ex. XXI | 100 | 92 | 35 | 7 |
| Prod. of Ex. XXII | 84 | 58 | 52 | 3 |
| Prod. of Ex. XXIII | 59 | 96 | 91 | 84 |
| Prod. of Ex. XXIV | 85 | 90 | 78 | 81 |
| Prod. of Ex. XXV | 73 | 81 | 77 | 64 |
| Prod. of Ex. XXVI | 72 | 49 | 5 | 0 |
| Prod. of Ex. XXVII | 87 | 85 | 52 | 6 |
| Prod. of Ex. XXVIII | 74 | — | — | — |
| Prod. of Ex. XXX | 87 | 80 | 64 | 16 |
| Prod. of Ex. XXXI | 85 | 74 | 74 | 28 |
| Prod. of Ex. XXXII | 94 | 69 | 31 | 2 |
| Prod. of Ex. XXXIII | 81 | 64 | 22 | 4 |
| Prod. of Ex. XXXIV | 71 | 84 | 54 | 17 |

EXAMPLE XLI

The following spiro-hydantoin compounds of Preparation C and Examples I-V, VII-IX, XI-XVII, XIX-XXV, XXVII and XXX-XXXIII, respectively, were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50-100 mM/g. tissue to as high as 400 mM/g. tissue in the 27-hour test period):

| Compound | Percent Inhibition (%) | | | | |
|---|---|---|---|---|---|
| | 0.75 | 1.5 | 2.5 | 5.0 | 10 mg./kg. |
| Prod. of Prep C | — | — | — | 3 | 40 |
| Prod. of Ex. I | — | 29 | — | 52 | 67 |
| Prod. of Ex. II | — | — | — | 6 | 54 |
| Prod. of Ex. III | — | — | — | 45 | — |
| Prod. of Ex. IV | — | — | — | 33 | 49 |
| Prod. of Ex. V | — | — | — | 9 | — |
| Prod. of Ex. VII | — | — | — | 39 | 65 |
| Prod. of Ex. VIII | — | — | — | 26 | — |
| Prod. of Ex. IX | — | — | 58 | — | — |
| Prod. of Ex. XI | — | — | — | 59 | — |
| Prod. of Ex. XII | 13 | 45 | 74 | — | — |
| Prod. of Ex. XIII | — | 5 | — | — | — |
| Prod. of Ex. XIV | — | 26 | — | — | — |
| Prod. of Ex. XV | — | — | — | 5 | 52 |
| Prod. of Ex. XVI | — | — | — | 25 | 44 |
| Prod. of Ex. XVII | — | — | — | — | 3 |
| Prod. of Ex. XIX | — | — | — | — | 15 |
| Prod. of Ex. XX | — | — | 34 | 58 | 77 |
| Prod. of Ex. XXI | — | — | 24 | — | — |
| Prod. of Ex. XXII | 45 | 72 | — | — | — |
| Prod. of Ex. XXIII | — | 64 | — | — | — |
| Prod. of Ex. XXIV | 82 | — | — | — | — |
| Prod. of Ex. XXV | 64 | 84 | — | — | — |
| Prod. of Ex. XXVII | — | 30 | — | — | — |
| Prod. of Ex. XXX | — | 35 | — | — | — |
| Prod. of Ex. XXXI | — | — | 47 | 68 | — |
| Prod. of Ex. XXXII | 28 | — | 12 | — | — |
| Prod. of Ex. XXXIII | — | — | — | 5 | — |

EXAMPLE XLII

6-Fluoro-spiro-[chroman-4,4'-imidazolidine]-2',5'-dione (the product of Example XXII) was tested for its ability to reverse already-elevated sorbitol levels in streptozotocin-induced diabetic rats of two weeks duration (i.e., chronic) by administering said compound orally to the animals for a period of seven days. In this study, the sorbitol determinations were carried out in both the sciatic nerve and the lens. Streptozotocin was first administered to the animals at 65 mg./kg., via the intravenous route. The animals then remained untreated for a period of two weeks. At the end of this time, a "control" group of eight rats (Control Group I) was sacrificed for baseline sorbitol determinations, while the remaining two groups of seven animals each either received 6-fluoro-spiro-[chroman-4,4'-imidazolidine]-2',5'-dione at 2.5 mg./kg., twice a day, or simply water alone (Control Group II). After seven days, the rats were sacrificed (three hours post dose) and it was found that while sciatic nerve sorbitol levels in the control group (Control Group II) had risen slightly above baseline values and lens sorbitol values had stabilized with respect to same, substantial reductions in sorbitol levels had occurred in both the sciatic nerve (68%) and lens (71%) of the treated group (i.e., those animals receiving the aforesaid test compound).

EXAMPLE XLIII

The ability of 6-fluoro-spiro-[chroman-4,4'-imidazolidine]-2',5'-dione to prevent or inhibit galactitol formation in acutely galactosemic rats was determined by administering said compound to the animals, via their feed, for a period of seven days. In this study, normal male rats were first divided into groups of six animals each and then fed a 30% galactose diet together with the compound to be administered at three different dosage levels. One group of animals received 6-fluoro-spiro-[chroman-4,4'-imidazolidine]-2',5'-dione at 10 mg./kg. and another at 20 mg./kg., respectively. A control group of nine animals received a 30% galactose diet without any compound. At the end of the seven-day period, lenses were removed for galactitol determination and it was found that while polyol levels in the control group had risen from essentially undetectable amounts to a value of well over 30 μmoles/g., in those rats receiving the test compound in the diet in addition to galactose, there was definitely a very pronounced inhibition of galactitol values at the two higher dose levels tested (e.g., 72% at 20 mg./kg. and 40% at 10 mg./kg., respectively).

EXAMPLE XLIV

To determine the effect of 6-fluoro-spiro-[chroman-4,4'-imidazolidine]-2',5'-dione on cataract formation in galactosemia, rats were fed a 30% galactose diet with and without this compound for a period of 29 days and eye examinations were also routinely conducted approximately twice a week throughout this period. The experimental animals received the test compound mixed in the food at concentration levels necessary to afford approximate doses of 10 mg./kg. and 20 mg./kg., respectively. Control animals received the galactose diet alone (i.e., without the compound). After 8–14 days, it was found that lenticular opacities had developed in 90% of the eyes of the control animals as compared to no opacities being present in the cases of those rats receiving 6-fluoro-spiro-[chroman-4,4'-imidazolidine]-2',5'-dione at either 10 mg./kg. or 20 mg./kg., as aforesaid. At the end of 17 days, it was found that opacities were present in 100% of the eyes of the control animals, while only 6% of the eyes of those rats receiving 6-fluoro-spiro-[chroman-4,4'-imidazolidine]-2',5'-dione at 10 mg./kg. were actually affected. The corresponding value obtained in rats receiving the test compound at 20 mg./kg. was 0%. This delay in cataract formation continued in all the treated groups until the 22-day mark, at which point lenticular opacities were observed in greater than 90% of the eyes of those animals receiving the test compound at the 10 mg./kg. dose level. However, in rats receiving 6-fluoro-spiro-[chroman-4,4'-imidazolidine]-2',5'-dione at 20 mg./kg., an impressive delay in cataract formation was still observed at the 29-day mark, as evidenced by the fact that only 37% of the eyes of the animals in the treated group showed lenticular opacities.

EXAMPLE XLV

The effectiveness of 6-fluoro-spiro-[chroman-4,4'-imidazolidine]-2',5'-dione in delaying cataract development in rats is further highlighted by the test procedure of Example XLIV by giving careful consideration to the severity of the lenticular opacities involed. In this study, the percentage of lens areas involved were monitored throughout the 29-day period and the results obtained served as an index of severity. In this way, it was found that after 17 days, 75% of the control lenses involved showed an area of involvement which was never less than 10%. On the other hand, corresponding values of 6% and 0% were respectively obtained in the case of those rats receiving 6-fluoro-spiro-[chroman-4,4'-imidazolidine]-2',5'-dione at 10 mg./kg. and 20 mg./kg. dose levels. As a matter of fact, the severity of lenticular opacities in the treated groups was always less than that found in the control group, including the values obtained at the end of the 29-day mark.

EXAMPLE XLVI

The compounds prepared in Example XXXV are subjected to the test procedure of Example XL and are active as aldose reductase inhibitors at doses corresponding to at least one of the concentration levels previously indicated.

What is claimed is:

1. A method of treating a diabetic host to prevent or alleviate ocular and neuritic diabetes-associated chronic complications, which comprises orally, parenterally or topically administering to said host an effective amount of a compound selected from the group consisting of those of the formulae:

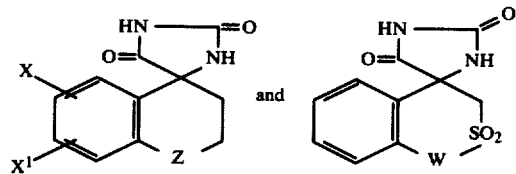

and the base salts thereof with pharmacologically acceptable cations, wherein

W is $-(CH_2)_n-$;

X is hydrogen and $X^1$ is hydrogen, hydroxy, fluorine, chlorine, bromine, lower alkyl or lower alkoxy; or $X$ and $X^1$, when taken separately, are each chlorine, lower alkyl or lower alkoxy and when taken together are $-OCH_2(CH_2)_nO-$;

Y is oxygen or sulfur;

Z is Y or Q wherein Q is

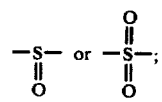

and n is zero or one.

2. The method as claimed in claim 1 wherein the compound administered is 6-fluoro-spiro-[chroman-4,4'-imidazolidine]-2',5'-dione.

3. The method as claimed in claim 1 wherein the compound administered is 6-chloro-spiro-[chroman-4,4'-imidazolidine]-2',5'-dione.

4. The method as claimed in claim 1 wherein the compound administered is 6,8-dichloro-spiro-[chroman-4,4'-imidazolidine]-2',5'-dione.

5. The method as claimed in claim 1 wherein the compound administered is 6,7-dichloro-spiro-[chroman-4,4'-imidazolidine]-2',5'-dione.

6. The method as claimed in claim 1 wherein the compound administered is 6'-fluoro-spiro-[imidazolidine-4,4'-thiochroman]-2,5-dione.

7. The method as claimed in claim 1 wherein the compound administered is 6',7'-dichloro-spiro-[imidazolidine-4,4'-thiochroman]-2,5'-dione.

* * * * *